United States Patent
Yu et al.

(10) Patent No.: US 8,619,253 B2
(45) Date of Patent: Dec. 31, 2013

(54) MULTI-PARAMETER INTEGRATED CUVETTE POOL

(75) Inventors: Aimin Yu, Changchun (CN); Zhende Wang, Changchun (CN)

(73) Assignee: Changchun Jilin University Little Swan Instruments Co., Ltd., Jilin (CN)

( * ) Notice: Subject to any disclaimer, the term of this patent is extended or adjusted under 35 U.S.C. 154(b) by 0 days.

(21) Appl. No.: 13/056,863

(22) PCT Filed: Dec. 9, 2009

(86) PCT No.: PCT/CN2009/001396
§ 371 (c)(1),
(2), (4) Date: Jan. 31, 2011

(87) PCT Pub. No.: WO2010/148545
PCT Pub. Date: Dec. 29, 2010

(65) Prior Publication Data
US 2012/0092659 A1    Apr. 19, 2012

(30) Foreign Application Priority Data
Jun. 25, 2009   (CN) .......................... 2009 1 0087913

(51) Int. Cl.
*G01N 1/10* (2006.01)
*G01N 33/48* (2006.01)

(52) U.S. Cl.
USPC ........................................ 356/246; 356/39

(58) Field of Classification Search
USPC .......... 356/244, 346, 311, 347, 437, 439, 440
See application file for complete search history.

(56) References Cited

U.S. PATENT DOCUMENTS

| | | | |
|---|---|---|---|
| 4,682,890 A * | 7/1987 | de Macario et al. | 356/244 |
| 5,098,661 A * | 3/1992 | Froehlich et al. | 356/246 |
| 5,658,532 A * | 8/1997 | Kurosaki et al. | 422/64 |
| 7,674,430 B2 * | 3/2010 | Ouchi et al. | 422/67 |
| 2008/0293091 A1* | 11/2008 | Kanipayor et al. | 435/29 |
| 2010/0124758 A1* | 5/2010 | Hoehl et al. | 435/26 |

FOREIGN PATENT DOCUMENTS

| | | |
|---|---|---|
| CN | 2611904 Y | 4/2004 |
| CN | 200965515 Y | 10/2007 |
| CN | 101281121 A | 10/2008 |
| CN | 101581661 A | 11/2009 |
| EP | 0195769 A | 9/1986 |
| GB | 1144408 A | 3/1969 |
| JP | 61160040 A | 7/1986 |

* cited by examiner

*Primary Examiner* — Gregory J Toatley
*Assistant Examiner* — Sunghee Y Gray
(74) *Attorney, Agent, or Firm* — Troutman Sanders LLP

(57) ABSTRACT

The invention provides a multi-parameter integrated cuvette pool having a plurality of cuvette pool cells. Adjacent cuvette pool cells are connected to each other through a connecting plate. A heat generation unit is arranged in each cuvette pool cell.

4 Claims, 3 Drawing Sheets

MULTI-PARAMETER INTEGRATED CUVETTE POOL

INCORPORATION BY REFERENCE

The application is a 371 of International Application No. PCT/CN2009/001396 filed Dec. 9, 2009, which claims priority to Chinese Patent Application No. 200910087913.0 filed Jun. 25, 2009, the entire contents of which being hereby incorporated herein by reference.

FIELD OF THE INVENTION

The invention relates to a component applied in a photometric analyzer, in particular to a long-life, stable, and accurate multi-parameter integrated cuvette pool, which is a replacement of the assembly of a conventional cuvette pool and a heater.

BACKGROUND OF THE INVENTION

Spectrophotometry is an analytical method established on the basis of selective light absorption of materials, and is one of popular instrumental analysis methods at present. The theoretical foundation of spectrophotometry is the Lambert-Beer Law. Usually, a sample to be tested is loaded into a cuvette, and then the cuvette is loaded into a cuvette pool in an apparatus for detection, data acquisition and transmission. Since different chemical reactions require different conditions, some color reactions have high requirements for temperature. Usually, the tester has to load the cuvette containing the sample to be tested into a heater and heat up to a specific temperature; then, the tester has to take out the cuvette and load it into a cuvette pool to perform sample detection. Such an approach results in temperature change in the cuvette and is not convenient. Moreover, the existing detections are generally restricted to detections of a single parameter of a single sample. When detection of parameters of several samples or several parameters of the same sample is required. the operating cycle has to be repeated. During parallel detection or comparative detection, different heating and detection cycles may easily cause error and degrade the accuracy of detection.

SUMMARY OF THE INVENTION

In view of the above problems, the invention provides a multi-parameter integrated cuvette pool that can serve as both a cuvette pool and a heater in a photometric analyzer.

To attain the object described above, the invention provides a multi-parameter integrated cuvette pool having a plurality of cuvette pool cells, wherein adjacent cuvette pool cells are connected to each other through a connecting plate, and a heat generation unit is arranged in each cuvette pool cell.

A light source inlet for installing a light source is arranged on a side wall of the cuvette pool cell, and a photoelectric sensor receiving port for installing a photoelectric sensor is arranged at a corresponding position on the opposite side wall of the cuvette pool cell.

A cuvette inlet is arranged to protrude upwardly at the center of an upper cover of the cuvette pool cell, and a notch for positioning the cuvette is arranged on the upper edge of the cuvette inlet.

The heat generation unit is a heating element, which fits tightly to the side wall of a cavity of the cuvette pool cell, and matches the cuvette in shape. On the heat generation unit, an inlet is arranged at the position of light source inlet, and a receiving port is arranged at the position of sensor receiving port.

Alternatively, the heat generation unit is composed of a heat-conducting element and a heat source, wherein the heat-conducting element fits tightly to the side wall and bottom of the cavity of the cuvette pool cell, extends out of the cuvette pool cell and connects with the heat source, and matches the cuvette in shape. In addition, on the heating element, an inlet is arranged at the position of the light source inlet, and a receiving port is arranged at the position of the sensor receiving port. The heat-conducting elements of a plurality of cuvette pool cells share the same heat source.

Another object of the invention is to provide a method for detecting multiple parameters of a sample by using a photometric analyzer. In the method provided in the invention, the integrated cuvette pool described above is used in a cuvette rack of a photometric analyzer, a light source in a specific wavelength is mounted in each cuvette pool cell, and the light sources in different cuvette pool cells are different in wavelength. The same sample is loaded into each cuvette pool cell, several cuvette pool cells are simultaneously loaded side by side into the cuvette rack of the photometric analyzer for detection. Such an arrangement is applicable to measurement of several parameters of the same sample.

In another method for detecting multiple samples by using a photometric analyzer in the invention, the integrated cuvette pool described above is used in a cuvette rack of a photometric analyzer, a light source in the same wavelength is mounted in each cuvette pool cell, and a different sample is loaded into each cuvette pool cell. Several cuvette pool cells are simultaneously loaded side by side into the cuvette rack of the photometric analyzer for detection. Such an arrangement is applicable to measurement of the same parameter among multiple samples.

In the invention, the multi-parameter integrated cuvette pool is formed by a plurality of separate cuvette pool cells with cuvette pool function which are molded into one piece, and the connecting portion between adjacent cuvette pool cells can be broken. Therefore, the cuvette pool can be composed of any number of cuvette pool cells. Each cuvette pool cell has a heating element or heat-conducting element, and the temperature in each cuvette pool cell can be set separately or set to be the same temperature among the cuvette pool cells. Therefore, the cuvette pool is applicable to multi-parameter measurement.

The interior of the cuvette pool is circular or rectangular in shape, depending on the shape of cuvettes used; a light source inlet is arranged on one side of the cuvette pool, and a detector receiving port is arranged on the opposite side of the cuvette pool at a position in alignment with the light source inlet. The heating element is a ceramic heating element, and its temperature is controllable. The heating element is in a shape matching the cuvette, and fit tightly to the cuvette pool. Therefore, the cuvette pool is applicable to multi-parameter measurement at the same temperature or different temperatures.

In the invention, the heat-conducting element is made of copper or other materials with high heat conduction coefficient. Different cuvette pool cells can share the same heat source. The cuvette pool has better efficacy for parallel detection of the same sample in multiple cuvettes at the same temperature.

The invention has the following advantages:

1. The cuvette pool supports integrated multi-parameter detection and can be composed of any number of cuvette pool cells, and therefore has a wide scope of application.

2. The heating temperature in the cuvette pool can be set freely; therefore, the cuvette pool is highly practical.

3. The cuvette pool serves as both a cuvette pool and a heater, and is convenient to use.

4. The integrated cuvette pool in accordance with the invention can reduce the troubles resulted from intermittent heating, and improve the efficacy of the analyzer.

5. The multi-parameter integrated cuvette pool has a long service life, high stability, and high accuracy, and is a replacement for the assembly of a cuvette pool and a heater. The invention can improve reliability and measurement accuracy of the analyzer.

DETAILED DESCRIPTION OF THE EMBODIMENTS

Hereunder embodiments of the invention will be described, with reference to the accompanying drawings.

The invention is a special analytical component designed on the theoretical basis of spectrophotometry.

Figure 1:
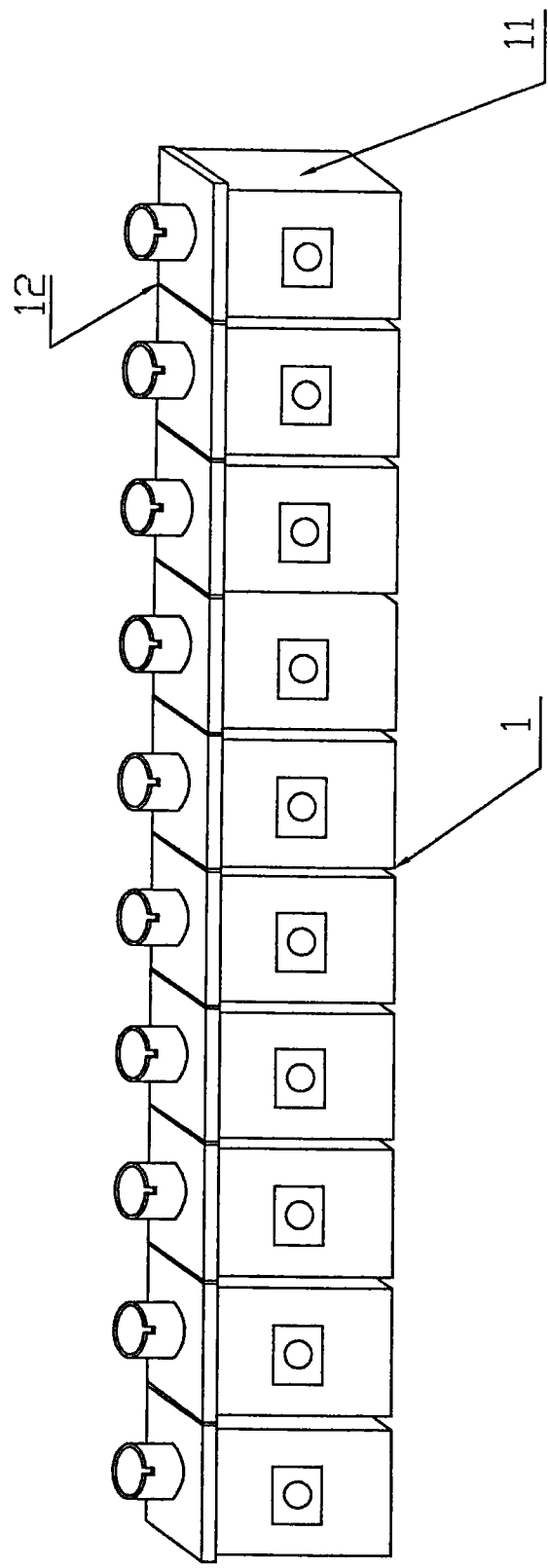
FIG. 1 is a perspective view of an external structure of a multi-parameter integrated cuvette pool provided in the invention.

A multi-parameter integrated cuvette pool 1 in the invention is composed of an assembly of a plurality of cuvette pool cells 11. FIG. 1 shows an integrated cuvette pool 1 formed by connecting ten cuvette pool cells 11 sequentially, wherein adjacent cuvette pool cells 11 are connected to each other through a connecting plate 12, which can be broken and can be made of plastic material. Each cuvette pool cell 11 has cuvette pool function and is equipped with a heat generation unit, which is to say, each cuvette pool cell serves as both a cuvette pool and a heater. In addition, the multi-parameter integrated cuvette pool in the invention can be composed of any number of cuvette pool cells 11.

Figure 2A:
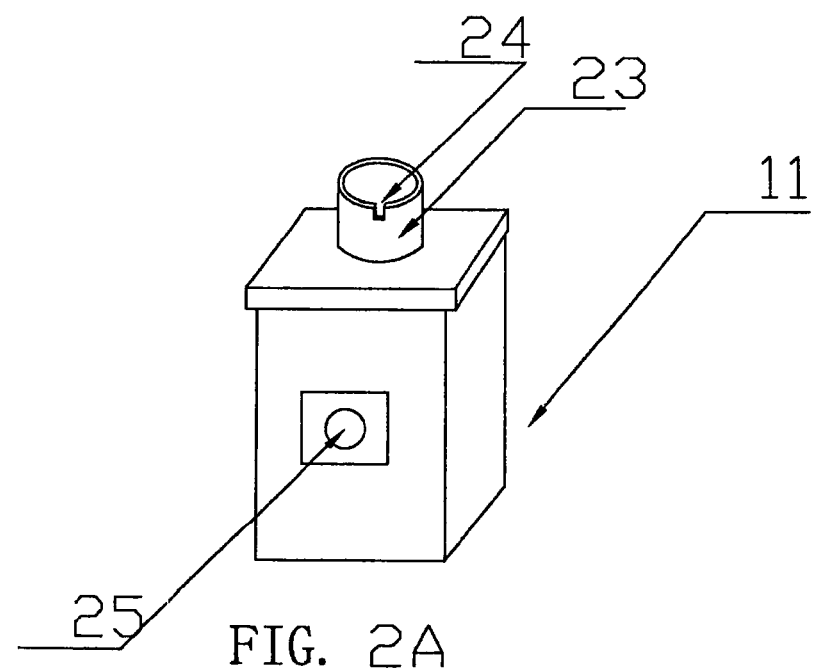
FIG. 2A is a perspective view of an external structure of a cuvette pool cell in the invention.
Figure 2B:
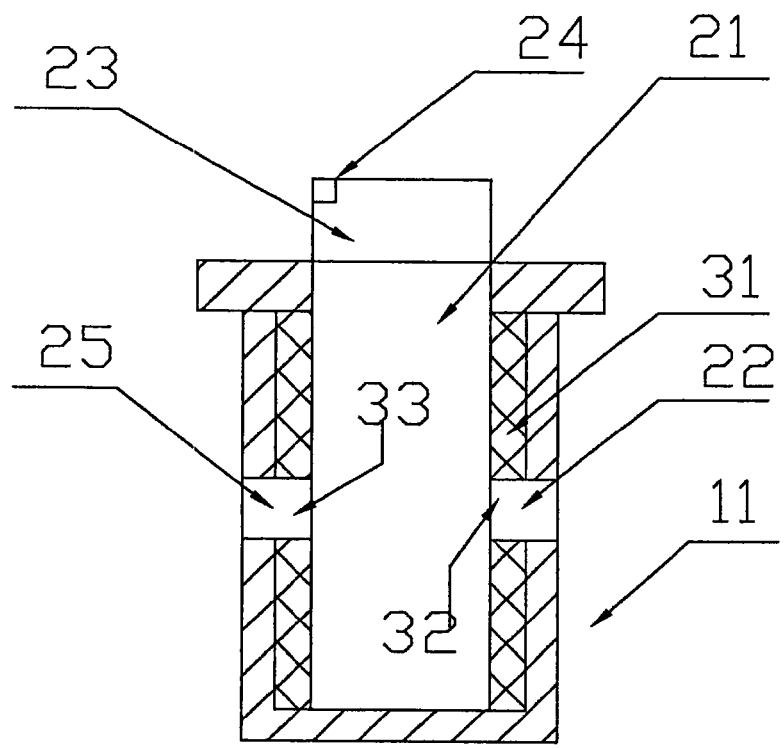
FIG. 2B is a sectional view of an internal structure of the cuvette pool cell in the invention.

As shown in FIG. 2A and FIG. 2B, the cuvette pool cell 11 has a groove shaped cavity 21, which can be circular or rectangular in shape, depending on the shape of the cuvette used. In the cavity 21, a heating element 31 (heat generation unit) is fitted tightly to the inner sidewall of the cuvette pool cell 11. A light source inlet 22 for mounting a light source is arranged on a side wall of the cuvette pool cell 11, and a sensor receiving port 25 for mounting a photoelectric sensor is arranged at the position corresponding to the light source inlet 22 on the opposite sidewall of the cuvette pool cell 11. A cuvette inlet 23 is arranged to protrude upwardly at the center of the upper cover of the cuvette pool cell 11, and a notch is arranged on the upper edge of the cuvette inlet 23 and serves as a cuvette positioning notch 24.

During sample detection, the cuvette is inserted from top to bottom into the cavity 21 of the cuvette pool through the cuvette inlet 23, and the cuvette is positioned in the cuvette pool cell 11 by means of the cuvette positioning notch 24. The cuvette pool cells 11 to be detected are loaded into a detection instrument (photometric analyzer), the heating elements 31 inside the cuvette pool cells 11 heat up the samples in the cuvettes to a specified temperature, and then the samples are detected by the detection instrument.

In the invention, the light source can be made of ultra high brightness LEDs, and serves as both a light source of the detection instrument and a monochromator. The photoelectric sensor is a photoelectric detector of the detection instrument. Each cuvette pool cell 11 has a light source that emits light in a single wavelength and a photoelectric detector corresponding to the light source. The light sources mounted in different cuvette pool cells 11 may be in the same wavelength or different wavelengths. When several parameters of the same sample are to be detected, an integrated cuvette pool in which each of the cuvette pool cells has a light source in a different wavelength can be used. When the same parameter among several samples is to be detected, an integrated cuvette pool with light sources in the same wavelength mounted in the cuvette pool cells can be used. In that way, with the integrated cuvette pool provided in the invention, the cuvette pool cells can be combined as required, and multiple cuvette pool cells can be simultaneously loaded side by side into a cuvette rack in the photometric analyzer, so as to measure several parameters of the same sample or measure the same parameter among different samples.

Figure 3A:
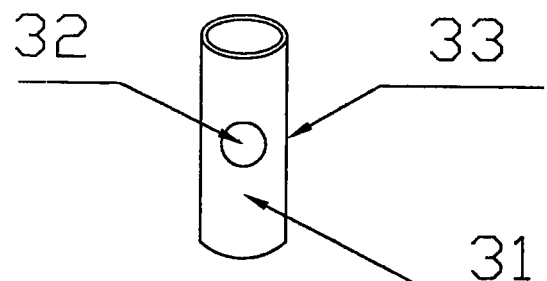
FIG. 3A is a perspective view of an external structure of a heating element used in the cuvette pool cell in the invention.

As for the design of the heat generation unit, in an embodiment of the invention shown in FIG. 3A, the heat generation unit is a ceramic heating element 31, with controllable heating temperature, in shape matching the cuvette used during the detection. In addition, on the heating element 31, an inlet 32 is arranged at the position of the light source inlet 22, and a receiving port 33 is arranged at the position of the sensor receiving port 25 (see FIG. 2B). The heating element 31 fits tightly to the cavity 21 of the cuvette pool. The heating element 31 is applicable to heating for multi-parameter detection at the same temperature or different temperatures.

Figure 3B:
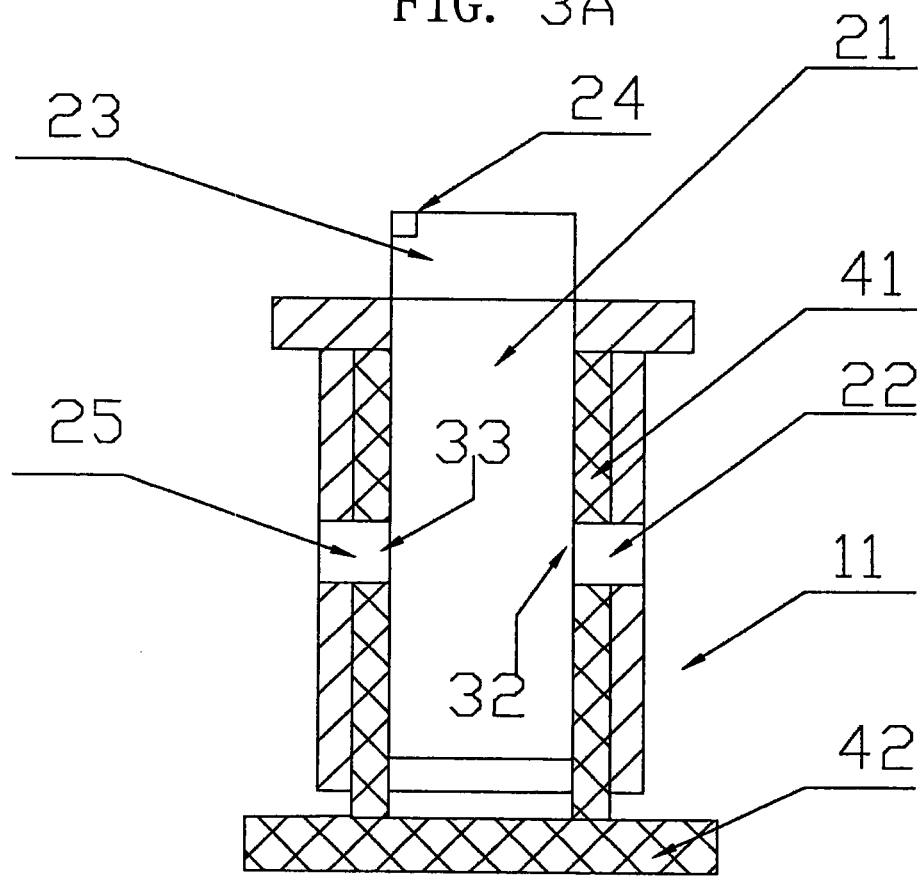
FIG. 3B is a structural diagram of a heat-conducting element used in the integrated cuvette pool in the invention.

In another embodiment, the heat generation unit can be composed of a heat-conducting element 41 and a heat source, as shown in FIG. 3B, wherein the heat-conducting element 41 is made of copper or other materials with high heat conduction coefficient, fits tightly to the sidewall of the cavity 21 of the cuvette pool cell 11, extends out of the cuvette pool cell 11 and connects with a heat source 42. The rest part of the heat-conducting element 41 is the same as the above mentioned heating element 31. When multiple cuvette pool cells 11 are used, the heat-conducting elements 41 can share the same heat source 42 (e.g., a heating aluminum plate). The heating aluminum plate can be directly arranged on the bottom or sidewall of a cuvette rack (the space for accommodating the cuvette pool in the detection instrument), the heat-conducting elements 41 in the cuvette pool cells 11 fits tightly to the heating aluminum plate, and the controlled temperature of the heating aluminum plate is transferred through the heat-conducting elements to each cuvette. Such an approach can improve the efficacy of parallel detection of multiple samples (loaded in cuvettes) at the same temperature for the same kind of sample.

The integrated cuvette pool described above is applicable to multi-parameter sample detection with a photometric analyzer. In such an detection process, the integrated cuvette pool is loaded into the cuvette rack of a photometric analyzer, a cuvette containing the same sample is loaded into each cuvette pool cell, a light source in a specific wavelength is mounted in each cuvette pool cell, and the light sources in different cuvette pool cells are different in wavelength. Several cuvette pool cells are simultaneously loaded side by side into the cuvette rack of the photometric analyzer for detection. Such an arrangement is applicable to measurement of several parameters of the same sample.

The integrated cuvette pool described above is also applicable to multi-sample detection with a photometric analyzer. In such a detection process, the integrated cuvette pool is loaded into the cuvette rack of a photometric analyzer, a light source in the same wavelength is mounted in each cuvette pool cell. A cuvette containing a different sample is loaded into each of the cuvette pool cells, and several cuvette pool cells are simultaneously loaded side by side into the cuvette rack of the photometric analyzer for detection. Such an arrangement is applicable to measurement of the same parameter among different samples.

INDUSTRIAL APPLICABILITY

The multi-parameter integrated cuvette pool provided in the invention is compact in structure and reasonable in design. It serves as both a cuvette pool and a heater and is used in a photometric analyzer, and can reduce the troubles resulted from intermittent heating. In addition, a plurality of cuvette pool cells can be integrated in any number into a cuvette pool; therefore, the cuvette pool is applicable to detection of several parameters of the same sample or detection of the same parameter among different samples in a photometric analyzer. The cuvette pool improves reliability of analysis and accuracy of measurement, and is suitable for industrial manufacturing and application.

The invention claimed is:

1. A multi-parameter integrated cuvette pool, comprising:
a plurality of cuvette pool cells, wherein
adjacent cuvette pool cells are connected to each other through a connecting plate,
a heat generation unit is provided in each of the plurality of cuvette pool cells,
a light source inlet for installing a light source is provided on a side wall of the cuvette pool cell, and a photoelectric sensor receiving port for installing a photoelectric sensor is provided at a corresponding position on an opposite side wall of the cuvette pool cell,
the heat generation unit includes a heat-conducting element and a heat source,
the heat-conducting element fits tightly to the sidewall and bottom of cavity of the cuvette pool cell, extends out of the cuvette pool cell and connects to the heat source, and matches the cuvette in shape, and
on the heating element, an inlet is provided at a position of the light source inlet, and a receiving port is provided at the position of the sensor receiving port.

2. The multi-parameter integrated cuvette pool according to claim 1, wherein the heat-conducting elements in the cuvette pool cells share the same heat source.

3. A method for detecting multiple parameters of a sample by using a photometric analyzer, comprising:
providing a multi-parameter integrated cuvette pool in a cuvette rack of a photometric analyzer, the multi-parameter integrated cuvette pool having
a plurality of cuvette pool cells, wherein
adjacent cuvette pool cells are connected to each other through a connecting plate,
a heat generation unit is provided in each of the cuvette pool cells,
a light source inlet for installing a light source is provided on a side wall of the cuvette pool cell, and a photoelectric sensor receiving port for installing a photoelectric sensor is provided at a corresponding position on an opposite side wall of the cuvette pool cell,
the heat generation unit includes a heat-conducting element and a heat source,
the heat-conducting element fits tightly to the sidewall and bottom of cavity of the cuvette pool cell, extends out of the cuvette pool cell and connects to the heat source, and matches the cuvette in shape, and
on the heating element, an inlet is provided at a position of the light source inlet, and a receiving port is provided at the position of the sensor receiving port;
mounting a light source in a specific wavelength in each of the cuvette pool cells, the light sources being in different wavelengths among the cuvette pool cells;
loading a same sample into each of the cuvette pool cells; and
simultaneously loading several cuvette pool cells side by side into the cuvette rack of the photometric analyzer for detection.

4. A method for detecting multiple samples by using a photometric analyzer, comprising:
providing a multi-parameter integrated cuvette pool in a cuvette rack of a photometric analyzer, the multi-parameter integrated cuvette pool having
a plurality of cuvette pool cells, wherein
adjacent cuvette pool cells are connected to each other through a connecting plate,
a heat generation unit is provided in each of the cuvette pool cells,
a light source inlet for installing a light source is provided on a side wall of the cuvette pool cell, and a photoelectric sensor receiving port for installing a photoelectric sensor is provided at a corresponding position on an opposite side wall of the cuvette pool cell,
the heat generation unit includes a heat-conducting element and a heat source,
the heat-conducting element fits tightly to the sidewall and bottom of cavity of the cuvette pool cell, extends out of the cuvette pool cell and connects to the heat source, and matches the cuvette in shape, and
on the heating element, an inlet is provided at a position of the light source inlet, and a receiving port is provided at the position of the sensor receiving port;
mounting a light source in a same wavelength in each of the cuvette pool cells;
loading a different sample into each of the cuvette pool cells; and
simultaneously loading several cuvette pool cells side by side into the cuvette rack of the photometric analyzer for detection.

* * * * *